United States Patent [19]

Rogic et al.

[11] B 3,991,113

[45] Nov. 9, 1976

[54] 2-ALKOXY-3-OXIMINOCYCLOALKENES AND PRODUCTION THEREOF

[75] Inventors: Milorad M. Rogic, Whippany; Robert Fuhrmann, Morris Plains, both of N.J.

[73] Assignee: Allied Chemical Corporation, Morris Township, N.J.

[22] Filed: Oct. 8, 1974

[21] Appl. No.: 513,014

[44] Published under the second Trial Voluntary Protest Program on February 10, 1976 as document No. B 513,014.

Related U.S. Application Data

[63] Continuation-in-part of Ser. No. 372,456, June 21, 1973, abandoned.

[52] U.S. Cl. .............................. 260/566 A; 424/327
[51] Int. Cl.² ........................................ C07C 131/08
[58] Field of Search .............................. 260/566 A

[56] References Cited
UNITED STATES PATENTS 3,857,510  12/1974  Rogic et al. .................... 260/566 A

*Primary Examiner*—Gerald A. Schwartz
*Attorney, Agent, or Firm*—Arthur J. Plantamura; Robert A. Harman

[57] ABSTRACT

Novel, 2-alkoxy-3-oximinocycloalkenes are prepared by nitrosating cycloalkanones in the presence of a polar nonbasic solvent, an alcohol and at least one equivalent of a strong acid.

6 Claims, No Drawings

2-ALKOXY-3-OXIMINOCYCLOALKENES AND PRODUCTION THEREOF

The present application is a continuation-in-part of application Ser. No. 372,456, filed June 21, 1973, now abandoned.

BACKGROUND OF THE INVENTION

1. Field of the Invention

This invention relates to novel 2-alkoxy-3-oximinocycloalkene compounds and acid salts thereof and to a method for their production. The 2-alkoxy-3-oximinocycloalkene compounds disclosed herein are represented by the following generic formula:

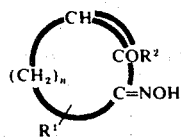

wherein $R^1$ is a substituent selected from the group consisting of hydrogen, or aliphatic $C_1$ to $C_{10}$ radicals; $R^2$ is the hydrocarbon radical of an aliphatic $C_1$ to $C_{10}$ alcohols or $C_5$-$C_6$ cyclic alcohol and n is an integer of from 2 to 9. These compounds are prepared by nitrosating the corresponding cyclic ketone in the presence of an inert solvent having a dielectric constant of at least about 12, such as sulfur dioxide, sulfolane nitromethane, or nitrobenzene, an aliphatic $C_1$ to $C_{10}$ alcohol or $C_5$-$C_6$ cyclic alcohol and at least one equivalent, preferably 2 to 5 equivalents, hydrochloric, hydrobromic, chlorosulfonic or strong Lewis acids such as borontrifluoride etherate or other strong mineral acid. These compounds are useful as fungicides and and precursors in the preparation of nylons or amino acids.

DESCRIPTION OF THE PRIOR ART

It is disclosed in our co-pending application Ser. No. 285,681 filed Sept. 1, 1972, now U.S. Pat. No. 3,857,510 that the carbon-carbon bond adjacent to a ketonic carbon can be cleaved with a nitrosating agent in the presence of alcohol and an aprotic solvent and in the absence of any supplemental acid. Nitrosation in the solvent system described in that application transforms the ketonic carbon into a terminal carboxylic acid ester group and an oxime group. Specifically, in the case of cyclic ketones, nitrosation in such a system results in the production of an ω-oximino acid ester.

Other previous attempts to nitrosate these cyclic ketones have resulted in the corresponding dinitrosated product, α,α'-dioximinocycloalkanones. Thus, heretofore an efficient process for the production of cyclic ketones which are directly mononitrosated without cleavage and which are desirable as synthetic intermediates was unknown in the art.

SUMMARY OF THE INVENTION

The present invention is related to 2-alkoxy-3-oximinocycloalkenes and to a method for their production which comprises admixing a ketone of the formula:

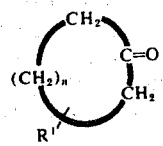

wherein n is an integer of from 2-9 and $R^1$ is a substituent selected from the group consisting of hydrogen, or an aliphatic $C_1$ to $C_{10}$ radicals, with a nitrosating agent in the presence of an inert solvent having a dielectric constant of at least about 12, such as sulfur dioxide, sulfolane, nitromethane or nitrobenzene, an aliphatic $C_1$ to $C_{10}$ or a cyclic $C_5$-$C_6$ alcohol and at least one equivalent of hydrogen chloride, hydrogen bromide, chlorosulfonic acid or other strong Lewis acid, such as borontrifluoride etherate. As a specific illustration, by using cyclohexanone as the starting ketone, methanol, nitrosyl chloride and hydrochloric acid in the method of the invention, the novel product 2-alkoxy-3-oximinocyclohexene, a precursor of lysine is obtained.

DETAILED DESCRIPTION OF THE INVENTION

In accordance with the procedures of the present invention, ketones are reacted with a nitrosating agent in an inert solvent having a dielectric constant of at least about 12, preferably sulfur dioxide, sulfolane, nitromethane, or nitrobenzene, in the presence of an aliphatic $C_1$ to $C_{10}$ or a cyclic $C_5$-$C_6$ alcohol and at least one equivalent of hydrogen chloride, hydrogen bromide, chlorosulfonic acid or strong Lewis acid such as borontrifluoride etherate.

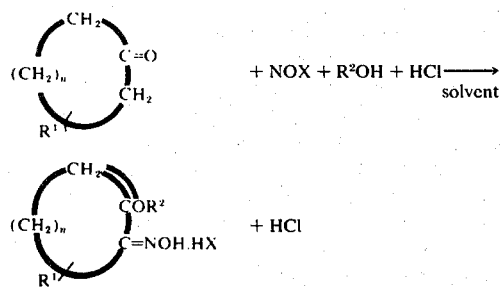

wherein $R^1$ is an aliphatic $C_1$-$C_{10}$ radical such as methyl, ethyl, n-propyl, isopropyl, t-butyl, isoamyl, decyl radical, $C_n$ is a hydrocarbon radical of 2 to 9 carbon atoms, e.g. 4-t-butylcyclohexanone ($n$=3), 6-ethylcyclododecanone ($n$=9), 6-n-decylcyclododecanone ($n$=9), X represents the acid radical of the nitrosating agent NOX, such as Cl, Br, $OSO_3H$, $BF_4$, and $R^2$ is the hydrocarbon radical of an aliphatic $C_1$-$C_{10}$ or cyclic $C_5$-$C_6$ alcohol such as methanol, ethanol, n-propanol, i-propanol, butyl alcohols, etc., or cyclopentanol or cyclohexanol. The corresponding 2-alkoxy-3-oximinocycloalkene is readily obtained as for example by treatment of the salt with various bases, such as $NH_3$, pyridine, amines, etc. or saturated $NaHCO_3$ solution or other alkalis followed by filtration.

The process of the present invention may be used to particular advantage in the case of cyclohexanone. For example, using nitrosyl chloride as the nitrosating agent, an alcohol, hydrogen chloride and liquid sulfur dioxide as the solvent, the reaction proceeds as follows:

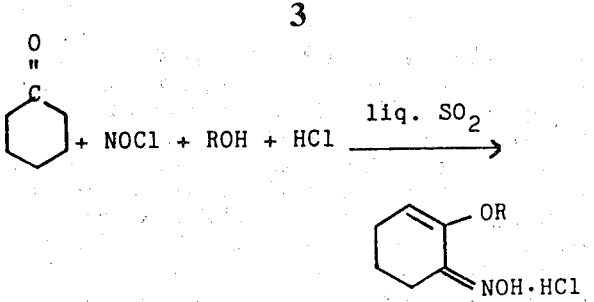

It is important to the success of the method of the present invention that the inert solvent employed should have a dielectric constant of at least 12 and be non-basic (i.e., the solvent should not be an electron pair donor in accordance with the concept of a Lewis base as described in Van der Werf in *Acids, Bases and the Chemistry of the Covalent Bond*, 1971, pages 60–71). If solvents possessing substantially different properties than those described above are employed, we have found that either the desired reaction does not take place, or numerous side products are also formed, thus making isolation difficult and providing poor yields. As a specific example, the use of diethyl ether or dimethyl ether of ethylene glycol does not lead to the desired product but rather to disubstitution and production of other by-products. Solvents suitable for use in the process of the present invention include sulfur dioxide, nitromethane, sulfolane, nitrobenzene, etc. Sulfur dioxide is preferred because it is non-flammable, inexpensive and a good solvent for both reactants and products. Additionally, because of its low boiling point, sulfur dioxide can be readily removed at low temperatures without need for provision for vacuum stripping.

Among the many nitrosating agents that can be used are the nitrosyl halides, such as NOCl, NOBr, and NOI; nitrosyl sulfuric acid ($NOOSO_3H$), nitrosyl formate, nitrosyl acetate, nitrosyl fluoroborate. These nitrosating agents may be formed by the known reaction of an alkyl nitrite and a suitable acid, preferably hydrogen chloride, hydrogen bromide or borontrifluoride etherate. Alternatively, the nitrosating agent can be formed in situ by adding the alkyl nitrite and acid to the reaction mixture. If an alkyl nitrite is used as the nitrosating agent, then the alkyl group should be the same as that of the alcohol used in the reaction, otherwise, a mixture of the product is formed corresponding to the different alkyl groups present. Although many nitrosating agents may be used with satisfactory results, nitrosyl chloride and nitrosyl tetrafluoroborate are the recommended agents.

The alcohol which is used, according to the process of the present invention, and which enters into the reaction and comprises the $R^2$ radical of the generic reaction previously given, may be an aliphatic $C_1$–$C_{10}$, or a cyclic $C_5$–$C_6$ alcohol. Preferably, an aliphatic alcohol, such as methanol, ethanol, isopropanol, butanols, isoamyl alcohol or 1-decanol having 1 to 10 carbon atoms inclusive are employed, and still more desirably, methanol or ethanol because of their low cost and high volatility.

As previously discussed, the novel compounds of the present invention are obtained only if the reactants include at least one mole acid per mole ketone. More acid could be used but no additional benefit would ensue. The acids which may be utilized to provide this essential environment include strong mineral acids, such as hydrochloric, hydrobromic, chlorosulfonic, a strong Lewis acid such as bromotrifluoride etherate. Because of its high volatility, hydrochloric acid is preferred since it can be readily removed from the reaction mixture after completion of the nitrosation. It is to be noted that if nitrosyl sulfuric acid is employed as the nitrosating agent in accordance with the procedures of the present invention, it will also function as the acidic agent since it imparts the required hydrogen ion to the system. However, because of the limited solubility of nitrosyl sulfuric acid in such solvents as $SO_2$, it may be necessary to add additional hydrochloric or other acid to suppress formation of the cleaved product or other undesired by-products.

The reaction of the present invention is carried out in sufficient amounts of the indicated solvents. Preferably, at least one mole each of nitrosating agent, alcohol and of acid should be present for each mole of ketone being nitrosated. The presence of substantially more than one mole of alcohol per mole of ketone is not harmful but serves no useful purpose. A large excess of nitrosating agent is undesirable since it can result in the formation of undesired by-products. Since the acid is recovered after completion of the reaction, it functions as a type of catalyst, promoting the nitrosation. In order to avoid side reactions, in particular cleavage of the cyclic ketone, the total amount of said acid added to the reaction mixture is at least one mole per mole ketone; larger amounts of acid could be used but would render recovery unnecessarily costly.

In some instances it may be desirable to regulate the order of addition so that the ketone and acid are not present in the mixture alone for an extended period of time during the reaction. Under these circumstances, a preferably order of addition would be to add the ketone to a mixture of the acid, nitrosating agent, alcohol and solvent. Optionally, the ketone and alcohol could be mixed with or without the addition of solvent and then added to a mixture of the nitrosating agent and acid in solvent. If all the reagents are liquid, they may be merely mixed in any of these preferred successions; if the nitrosation agent is gaseous, the other ingredients may be mixed and the gaseous nitrosation agent passed through the mixture.

The temperature at which the reaction is carried out is largely controlled by the choice of ketone, nitrosating agent and particularly the choice of solvent. Generally, the temperature will range between about −80° and +60°C., with a preferred range of −78° to +15°C. Since the reaction is exothermic, temperature control will be carried out with appropriate cooling.

The reaction time is dependent upon the temperature conditions. At ranges above about −10°C., the reaction takes place substantially as fast as the reactants are mixed so the time of reaction in the temperature range is not critical. Prolonged contact of the reactants is not harmful but serves no useful purpose. Completion of the reaction is most conveniently ascertained by vapor phase chromatographic analysis of an aliquot of the reaction mixture.

Recovery of the oximino enol ether salt after completion of the reaction is most advantageously carried out by evaporation of the solvent, any excess nitrosating agent, alcohol and acid. Since the salt obtained is a thermally unstable material, the work up should preferably be carried out at temperatures below about 0°C. If a nonvolatile acid was used, it must be otherwise removed from the reaction mixture or separated from the product by neutralization. The corresponding free oximino enol ether may then be obtained by the neutralization of the acid with ammonia, pyridine, saturated sodium bicarbonate solution or other suitable base.

The effect of the use of the indicated solvents together with alcohol and an excess of acid in promoting the desired reaction can be formulated as shown below. It is to be understood that we do not intend to confine our invention to any particular formulation or theory thereof. We postulate that solvents, such as sulfur dioxide offer particular stable environments for both the carbonium and nitrosonium ions. Thus, the solvent offers dual benefits by providing more active nitrosation species and by stabilizing the intermediate carbonium ion. The electrophilic attack of the nitrosation species on the double bond of the enol results in production of the corresponding carbonium ion intermediate. Then, the reaction of this intermediate 1-hydroxy-2-nitrosocycloalkane carbonium ion with the available neucleophilic alcohol provides the corresponding 1-hydroxy-1-alkoxy-2-nitrosocycloalkane which in the presence of the excess of acid undergoes isomerization to the corresponding oxime and after water elimination gives the acid salt of the 2-alkoxy-3-oximinocycloalkene compound. This series of reactions may be formulated as follows:

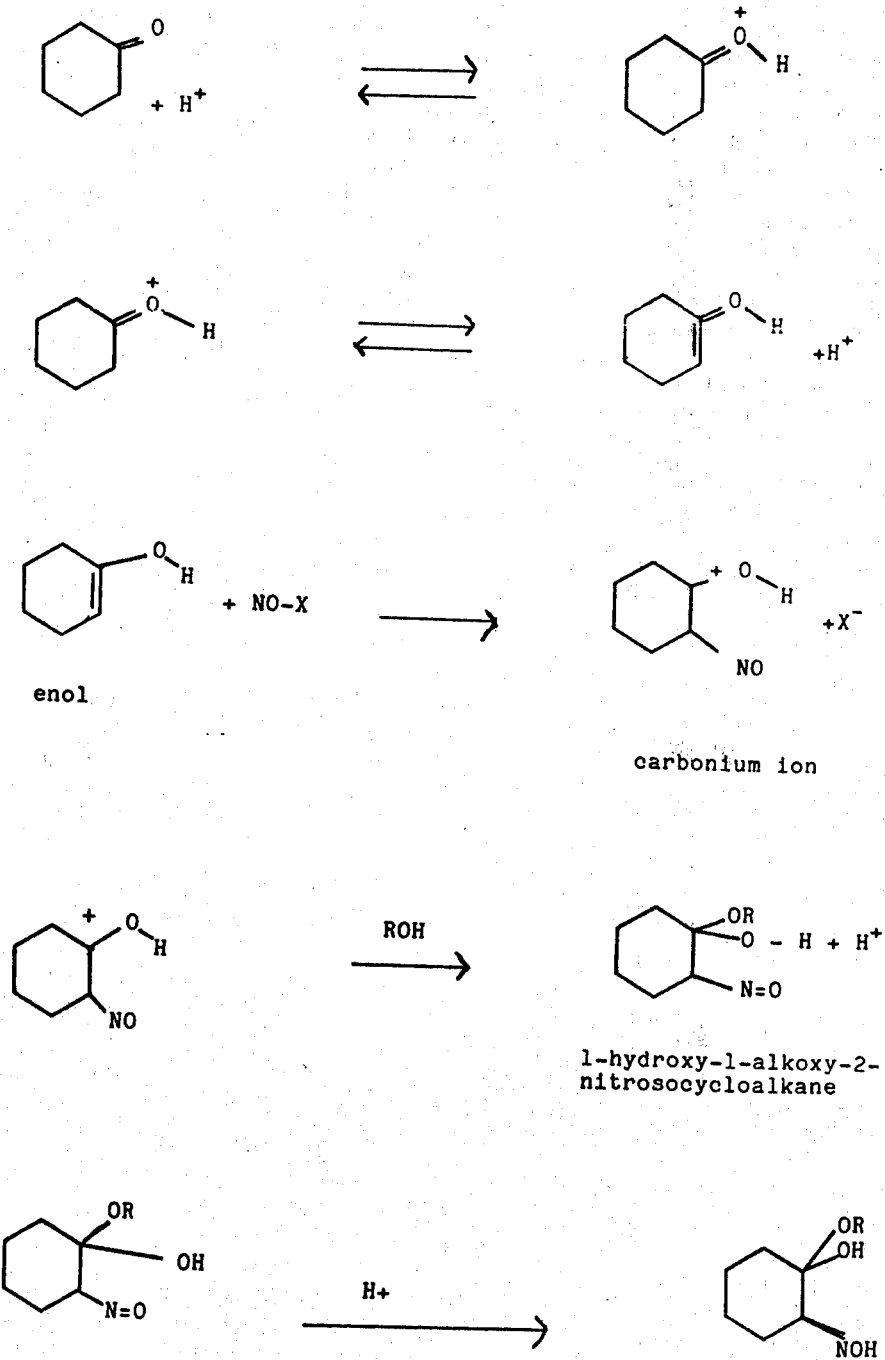

 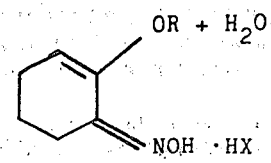

The invention can be more fully understood by reference to the following examples.

EXAMPLE 1

A three-neck 500 ml flask equipped with a mechanical stirrer, a dry ice condenser protected with a nitrogen bubbler, a dropping funnel, and an inlet tube, were placed in a dry ice bath. The inlet tube was connected to a sulfur dioxide cylinder and about 100 ml of sulfur dioxide was distilled into the flask. Using the same inlet tube, 200 mmol of dry hydrogen chloride gas was slowly introduced, which was then followed by 203 mmol (13.32 g) of nitrosyl chloride. The dropping funnel was charged with a solution of cyclohexanone (18.63 g, 190 mmol) in methanol (12.90 g, 403 mmol), which was added dropwise to the sulfur dioxide solution at −78°C. with stirring. The reaction mixture was stirred at the same temperature for approximately 30 minutes and then at reflux (−10°C) for 1 hour. After addition of pentane, sulfur dioxide and other low boiling materials were removed in vacuum at low temperature. The resulting white solid, weighing 61.2 g was treated with methanol and further evaporated to dryness. The material was then neutralized with 100 ml. water and 27.2 g $NaHCO_3$ to a pH of 6.5–7. After further washing with petroleum ether and drying, 24.5 grams product was obtained. The dried product had a melting point of 137°–140°C. and the spectral and analytical data identified the structure as 2-methoxy-3-oximinocyclohexene.

EXAMPLES 2–6

Using the nitrosating technique of Example 1, other cyclic ketones were converted into the corresponding oximino enol ethers. The results are tabulated below:

TABLE I

| Example | Ketone | Product |
|---|---|---|
| 2 | cyclopentanone | 2-methoxy-3-oximinocyclopentene |
| 3 | cycloheptanone | 2-methoxy-3-oximinocycloheptene |
| 4 | cyclooctanone | 2-methoxy-3-oximinocyclooctene |
| 5 | cyclododecanone | 2-methoxy-3-oximinocyclododecene |
| 6 | 4-t-butylcyclohexanone | 2-methoxy-3-oximino-4-t-butylcyclohexene |

EXAMPLES 7–12

Various alcohols can be used as illustrated by the reaction of cyclohexanone under the same reaction conditions as those given in Example 1. The results are as follows:

TABLE II

| Ex. | Alcohol | Product |
|---|---|---|
| 7 | ethanol | 2-ethoxy-3-oximinocyclohexene |
| 8 | n-propanol | 2-n-propoxy-3-oximinocyclohexene |
| 9 | i-propanol | 2-i-propoxy-3-oximinocyclohexene |
| 10 | n-butanol | 2-n-butoxy-3-oximinocyclohexene |
| 11 | i-butanol | 2-i-butoxy-3-oximinocyclohexene |
| 12 | benzyl alcohol | 2-phenyl-methoxy-3-oximinocyclohexene |

EXAMPLE 13

Although NOCl or similar nitrosyl halides are the preferred nitrosating agents, it is also possible to use nitrosyl sulfuric acid. Thus, Example 1 was repeated by nitrosating cyclohexanone with nitrosyl sulfuric acid in the presence of methyl alcohol in sulfur dioxide and one equivalent of borontrifluoride etherate and neutralizing the reaction mixture with $NH_3$ to obtain 2-methoxy-3-oximinocyclohexene.

EXAMPLE 14

The procedure of Example 1 was repeated using $BF_3 \cdot OEt_2$ as the acid catalyst in the presence of the solvent $SO_2$. Results were comparable to those in Example 1.

EXAMPLE 15

The procedure of Example 1 was repeated with the following exceptions. 4.9 G (50 mmol) cyclohexanone, 65 ml $SO_2$ and 4.2 g of a mixture of methanol and hydrochloric acid (containing 50 mmol HCl and 74 mmol MeOH) were first thoroughly combined at about −10°C. Then 4.9 g (76 mmol) NOCl was slowly introduced into the system which was maintained by use of reflux conditions at about −6°C. Addition of the NOCl was gradual over a period of about 30 minutes after which the acid salt was neutralized with pyridine. Gas chromatography indicated an 81% yield of the free 2-methoxy-3-oximinocyclohexene.

EXAMPLE 16

The procedure of Example 1 was repeated using two molar equivalents hydrochloric acid followed by the addition of one equivalent methyl nitrite. In this example, the nitrosyl chloride was formed in situ and methanol was produced as a by-product, thus providing the proper condition for the formation of the novel compound 2-methoxy-3-oximinocyclohexene.

EXAMPLE 17 (comparative)

In order to show the criticality of the addition of the acid catalyst to the formation of the novel products of the present invention, the procedure of Example 1 was followed using less than an equivalent of acid. Examination of the results indicated that the yield of the desired oximino enol ether product was proportionately reduced and the corresponding ω-oximino caproic acid ester was also produced.

We claim:

1. 2-Alkoxy-3-oximinocycloalkenes of the formula:

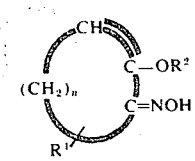

wherein $n$ is an integer 2–9, and $R^1$ is a member of the group consisting of hydrogen, aliphatic $C_1$–$C_{10}$ saturated hydrocarbon radicals and $R^2$ is an aliphatic $C_1$–$C_{10}$ saturated hydrocarbon radical or a cyclic aliphatic $C_5$–$C_6$ saturated hydrocarbon radical.

2. Acid salts of the 2-alkoxy-3-oximinocycloalkenes of claim 1 in which the acid is hydrochloric, hydrobromic, bromotrifluoride.

3. The compound of claim 1 wherein $n$ is 2.
4. The compound of claim 1 wherein $n$ is 3.
5. The compound of claim 1 wherein $n$ is 5.
6. The compound of claim 1 wherein $n$ is 9.

* * * * *

UNITED STATES PATENT AND TRADEMARK OFFICE
CERTIFICATE OF CORRECTION

PATENT NO. : 3,991,113
DATED : November 9, 1976
INVENTOR(S) : Milorad M. Rogic and Robert Fuhrmann It is certified that error appears in the above-identified patent and that said Letters Patent are hereby corrected as shown below:

Column 2, in the second part of the formula, change:

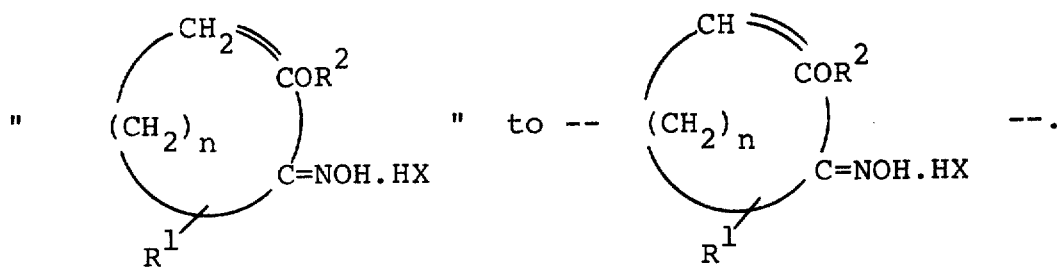

Column 10, line 2 change "bromotrifluoride" to -- borontrifluoride --.

Signed and Sealed this

First Day of March 1977

[SEAL]

Attest:

RUTH C. MASON
Attesting Officer

C. MARSHALL DANN
Commissioner of Patents and Trademarks